US009186719B2

(12) United States Patent
Bewlay et al.

(10) Patent No.: US 9,186,719 B2
(45) Date of Patent: Nov. 17, 2015

(54) CASTING MOLD COMPOSITION WITH IMPROVED DETECTABILITY FOR INCLUSIONS AND METHOD OF CASTING

(71) Applicant: GENERAL ELECTRIC COMPANY, Schenectady, NY (US)

(72) Inventors: Bernard Patrick Bewlay, Niskayuna, NY (US); Michael James Weimer, Loveland, OH (US); Joan McKiever, Ballston Lake, NY (US); Brian Michael Ellis, Mayfield, NY (US)

(73) Assignee: General Electric Company, Niskayuna, NY (US)

( * ) Notice: Subject to any disclaimer, the term of this patent is extended or adjusted under 35 U.S.C. 154(b) by 77 days.

(21) Appl. No.: 14/077,820

(22) Filed: Nov. 12, 2013

(65) Prior Publication Data
US 2014/0076512 A1 Mar. 20, 2014

Related U.S. Application Data

(62) Division of application No. 13/250,726, filed on Sep. 30, 2011, now Pat. No. 8,579,013.

(51) Int. Cl.
| | | |
|---|---|---|
| B22C 1/02 | (2006.01) |
| B22C 1/18 | (2006.01) |
| B22C 9/12 | (2006.01) |
| C04B 28/06 | (2006.01) |
| B22C 9/04 | (2006.01) |
| C04B 40/00 | (2006.01) |
| G01N 23/20 | (2006.01) |
| C04B 111/00 | (2006.01) |

(52) U.S. Cl.
CPC . *B22C 1/02* (2013.01); *B22C 1/181* (2013.01); *B22C 9/04* (2013.01); *B22C 9/12* (2013.01);

(Continued)

(58) Field of Classification Search
CPC .............. B22C 1/02; B22C 1/181; B22C 9/12
USPC ......... 164/4.1, 516–529; 106/38.2, 38.9, 638, 106/692
See application file for complete search history.

(56) References Cited

U.S. PATENT DOCUMENTS

| | | |
|---|---|---|
| 2,911,311 A | 11/1959 | Feagin et al. |
| 4,966,225 A | 10/1990 | Johnson et al. |

(Continued)

FOREIGN PATENT DOCUMENTS

WO   2010034765 A2   4/2010

OTHER PUBLICATIONS

Lyon et al., "The Interaction of Titanium with Refractory Oxides", The Interaction of Titanium With Refractory Oxides, pp. 271-284, 1973.

(Continued)

*Primary Examiner* — Kevin P Kerns
(74) *Attorney, Agent, or Firm* — John P. Darling

(57) ABSTRACT

A titanium-containing article casting mold composition includes calcium aluminate and an X-ray or Neutron-ray detectable element. A method for detecting sub-surface ceramic inclusions in a titanium or titanium alloy casting includes combining calcium aluminate, an element more radiographically dense than the calcium aluminate, and a liquid to form a slurry; forming a mold having the calcium aluminate and the radiographically dense element from the slurry; introducing a titanium aluminide-containing metal to the radiographically dense element-bearing mold; solidifying the titanium aluminide-containing metal to form an article in the mold; removing the solidified titanium aluminide-containing metal article from said mold; subjecting the solidified titanium aluminide-containing article to radiographic inspection to provide a radiograph; and examining the radiograph for the presence of the radiographically dense element on or in the article.

19 Claims, 10 Drawing Sheets

(52) U.S. Cl.
CPC ............ *C04B 28/06* (2013.01); *C04B 40/0096* (2013.01); *G01N 23/20* (2013.01); *C04B 2111/00215* (2013.01); *C04B 2111/00879* (2013.01); *C04B 2111/00939* (2013.01)

(56) References Cited

U.S. PATENT DOCUMENTS

| | | | |
|---|---|---|---|
| 5,297,615 | A | 3/1994 | Aimone et al. |
| 5,407,001 | A | 4/1995 | Yasrebi et al. |
| 5,626,179 | A | 5/1997 | Choudhury et al. |
| 5,678,298 | A | 10/1997 | Colvin et al. |
| 5,766,329 | A | 6/1998 | LaSalle et al. |
| 5,823,243 | A | 10/1998 | Kelly |
| 5,942,057 | A | 8/1999 | Hanamura et al. |
| 6,237,671 | B1 | 5/2001 | Lassow et al. |
| 6,619,368 | B1 * | 9/2003 | Springgate et al. ............ 164/4.1 |
| 8,579,013 | B2 * | 11/2013 | Bewlay et al. ................ 164/529 |
| 8,932,518 | B2 | 1/2015 | Bewlay et al. |
| 2004/0069434 | A1 | 4/2004 | Showman et al. |
| 2011/0203761 | A1 * | 8/2011 | Renkel ............................ 164/14 |

OTHER PUBLICATIONS

Konitzer et al., "Formation and Thermal Stability of an Oxide Dispersion in a Rapidly Solidified Ti—Er Alloy", Scripta Metallurgica, vol. No. 17, Issue No. 7, pp. 963-966, 1983.

Witt et al., "Titanium PM Components for Airframes," Conference—Titanium Net Shape Technologies, Los Angeles, California, USA, pp. 29-38, Feb. 26-Mar. 1, 1984.

Barnett, "Investment casting—the multi-process technology", Foundry International, vol. No. 11, Issue No. 3, Sep. 1988.

Saha et al., "On the Evaluation of Stability of Rare Earth Oxides as Face Coats for Investment Casting of Titanium", Metallurgical Transactions B, vol. No. 21B, pp. 559-566, Jun. 1990.

Cruz et al., "Effect of the ceramic mould composition on the surface quality of As-cast titanium alloy", Journal of Materials Science, vol. No. 40, Issue No. 22, pp. 6041-6043, Nov. 2005.

Non-Final Rejection towards corresponding U.S. Appl. No. 13/250,726 dated Aug. 8, 2012.

International Search Report and Written Opinion issued in connection with corresponding PCT Application No. PCT/US2012/053716 dated Jul. 22, 2013.

Unofficial English translation of Office Action issued in connection with corresponding CN Application No. 201280047731.0 on Jan. 29, 2015.

* cited by examiner

Backscattered electron images of the cross section of the mold fired at 1000 degrees celsius Calcium aluminate cement and fine-scale alumina particles The calcium aluminate cement in the fired mold contains calcium monoaluminate, calcium dialuminate, and minimal mayenite Backscattered electron images of the cross section of the mold fired at 1000 degrees celsius Backscattered electron images of the cross section of the mold fired at 1000 degrees celsius

| combining calcium aluminate, at least one element more radiographically dense than the calcium aluminate, and a liquid to form a slurry |
|---|
| forming a mold having the calcium aluminate and the radiographically dense element from the slurry |
| introducing a titanium aluminide-containing metal to the radiographically dense element-bearing mold |
| solidifying said titanium aluminide-containing metal to form an article in the mold |
| removing the solidified titanium aluminide-containing metal article from said mold |
| subjecting the solidified titanium aluminide-containing article to radiographic inspection to provide a radiograph |
| examining said radiograph for the presence of the radiographically dense element on or in the article |

FIGURE 9

CASTING MOLD COMPOSITION WITH IMPROVED DETECTABILITY FOR INCLUSIONS AND METHOD OF CASTING

CROSS-REFERENCE TO RELATED APPLICATION

This application is a division of U.S. patent application Ser. No. 13/250,726, now U.S. Pat. No. 8,579,013.

BACKGROUND

The present disclosure relates generally to casting mold compositions, and methods for casting titanium and titanium alloys.

Modern gas turbines, especially aircraft engines, must satisfy the highest demands with respect to reliability, weight, power, economy, and operating service life. In the development of aircraft engines, the material selection, the search for new suitable materials, as well as the search for new production methods, among other things, play an important role in meeting standards and satisfying the demand.

The materials used for aircraft engines or other gas turbines include titanium alloys, nickel alloys (also called super alloys) and high strength steels. Titanium alloys are generally used for compressor parts, nickel alloys are suitable for the hot parts of the aircraft engine, and the high strength steels are used, for example, for compressor housings and turbine housings. The highly loaded or stressed gas turbine components, such as, components for a compressor, for example, are forged parts. Components for a turbine, on the other hand, are typically fabricated as investment cast parts.

Although investment casting is not a new process, the investment casting market continues to grow as the demand for more intricate and complicated parts increase. Because of the great demand for high quality, precision castings, there continuously remains a need to develop new ways to make investment castings more quickly, efficiently, cheaply and of higher quality.

Conventional investment mold compounds that consist of fused silica, cristobalite, gypsum, or the like, that are used in casting jewelry and dental prostheses industries are not suitable for casting reactive alloys, such as titanium alloys. One reason is because there is a reaction between mold titanium and the investment mold. It is difficult to investment cast titanium and titanium alloys and similar reactive metals in ceramic molds because of the titanium's high affinity for elements such as, oxygen, nitrogen, and carbon. At elevated temperatures, titanium and its alloys can react with the mold facecoat.

The properties of the final casting are greatly deteriorated if any reaction occurs between the molten alloy and the mold. The form of this deterioration can include a poor surface finish due to gas bubbles, or in more serious cases, the chemistry, microstructure, and properties of the casting are compromised. Asperities and/or pits on the surfaces of cast alloy components can reduce aerodynamic performance in, for example, turbine blade applications, and increase wear and friction in rotating or reciprocating part applications. Therefore, there is a need in the art for new, practical and useful casting mold compositions and methods for detecting inclusions in reactive alloys, such as titanium alloys.

SUMMARY

Aspects of the present disclosure provide casting mold compositions, methods of casting, and cast articles that overcome the limitations of the state of the art. Some aspect of the disclosure may be directed toward the fabrication of components for the aerospace industry, for example, engine turbine blades. Further aspects may be employed in the fabrication of a component in any industry, in particular, those components containing titanium and/or titanium alloys.

One aspect of the disclosure is a mold composition for casting a titanium-containing article, comprising: a calcium aluminate cement comprising calcium monoaluminate, calcium dialuminate, and mayenite; and an X-ray or Neutron-ray detectable element. Another aspect of the present disclosure is a titanium-containing article casting-mold composition, comprising: calcium aluminate; and an X-ray or Neutron-ray detectable element. In one embodiment, the calcium aluminate cement forms an intrinsic facecoat of less than about 100 microns when the mold composition forms a mold. In one embodiment, the X-ray or Neutron-ray detectable elements are mixed within the mold. In another embodiment, the X-ray or Neutron-ray detectable elements are mixed within the mold and become part of the intrinsic facecoat. In one embodiment, the mold composition does not have an extrinsic facecoat.

In one embodiment, the mold composition further comprises oxide particles. The oxide particles may comprise at least one of aluminum oxide particles, magnesium oxide particles, calcium oxide particles, zirconium oxide particles, and titanium oxide particles. Moreover, in some instances, the oxide particles comprise hollow oxide particles, for example, the hollow oxide particles comprise hollow aluminum oxide particles. In a specific embodiment, the oxide particles are aluminum oxide particles.

In another embodiment, X-ray or Neutron-ray detectable element comprises ytterbium, hafnium, gadolinium, tungsten, thorium, uranium, yttrium, dysprosium, erbium, cerium, and compositions thereof. The X-ray or Neutron-ray detectable element may be in the range of about 1 to about 4 weight percent in the mold composition. The radiographically dense element may be more radiographically dense than the oxide particles. In one embodiment, radiographically dense element is more radiographically dense than calcium aluminate and comprises one or more of ytterbium, hafnium, gadolinium, tungsten, thorium, uranium, yttrium, dysprosium, erbium, cerium and compositions thereof.

One aspect of the present disclosure is a method for detecting sub-surface ceramic inclusions in a titanium or titanium alloy casting, said method comprising: combining calcium aluminate, at least one element more radiographically dense than the calcium aluminate, and a liquid to form a slurry; forming a mold having the calcium aluminate and the radiographically dense element from the slurry; introducing a titanium aluminide-containing metal to the radiographically dense element-bearing mold; solidifying said titanium aluminide-containing metal to form an article in the mold; removing the solidified titanium aluminide-containing metal article from said mold; subjecting the solidified titanium aluminide-containing article to radiographic inspection to provide a radiograph; and examining said radiograph for the presence of the radiographically dense element on or in the article.

In one embodiment, the method further comprises removing the radiographically dense element from the article. The removing the radiographically dense element from the article may comprise one or more steps of machining, grinding, polishing, or welding. The combining step may further comprise combining oxide particles with the slurry. In one embodiment, the oxide particles comprise hollow oxide particles, for example, hollow aluminum oxide particles.

In one embodiment, the method comprises minimizing the presence of mold material inclusions in titanium aluminide-containing cast articles. The titanium-containing cast article may comprise an engine or turbine, or a component of a turbine. For example, the titanium-containing cast article comprises a turbine blade. The titanium-containing cast article may be a titanium aluminide containing engine, a titanium aluminide containing turbine, or a titanium aluminide containing turbine blade.

One aspect of the present disclosure is a mold composition comprising: calcium aluminate cement comprising calcium monoaluminate, calcium dialuminate, and mayenite; and at least one element more radiographically dense than the calcium aluminate cement. Another aspect of the present disclosure is a mold composition comprising calcium aluminate and at least one element more radiographically dense than the calcium aluminate. In one embodiment, the mold composition further comprises oxide particles. In a related embodiment, the radiographically dense element is further more radiographically dense than the oxide particles.

Another aspect of the present disclosure is a mold composition for casting titanium-containing articles, comprising: calcium aluminate; and an X-ray or Neutron-ray detectable element. For instance, an aspect of the present disclosure may be uniquely suited to providing mold compositions to be used in molds for casting titanium-containing and/or titanium alloy-containing articles or components, for example, titanium containing turbine blades.

These and other aspects, features, and advantages of this disclosure will become apparent from the following detailed description of the various aspects of the disclosure taken in conjunction with the accompanying drawings.

BRIEF DESCRIPTION OF THE FIGURES

The subject matter, which is regarded as the invention, is particularly pointed out and distinctly claimed in the claims at the conclusion of the specification. The foregoing and other features and advantages of the present disclosure will be readily understood from the following detailed description of aspects of the disclosure taken in conjunction with the accompanying drawings in which:

FIG. 7a shows an X-ray image, with arrows pointing to examples of sub-surface inclusions and casting porosities. FIG. 7b is an zoomed in view of FIG. 7a. FIG. 7b shows an example of a sub-surface inclusion from the mold that is 5.44 mm in length. Casting porosities are also indicated, with one example the diameter of the porosity is indicated to be 0.99 mm.

FIG. 8a shows the mold with the intrinsic facecoat that is approximately 100 microns thick. The schematic shows the intrinsic facecoat with the mold cavity and calcium aluminate mold positions also indicated. FIG. 8b shows the mold with the extrinsic facecoat that is approximately 100 microns thick. The schematic shows the extrinsic facecoat with the mold cavity and calcium aluminate mold positions also indicated.

FIG. 9 shows a flow chart, in accordance with aspects of the disclosure, illustrating the steps of a method for detecting sub-surface ceramic inclusions in a titanium or titanium alloy casting.

DETAILED DESCRIPTION

Figure 1:
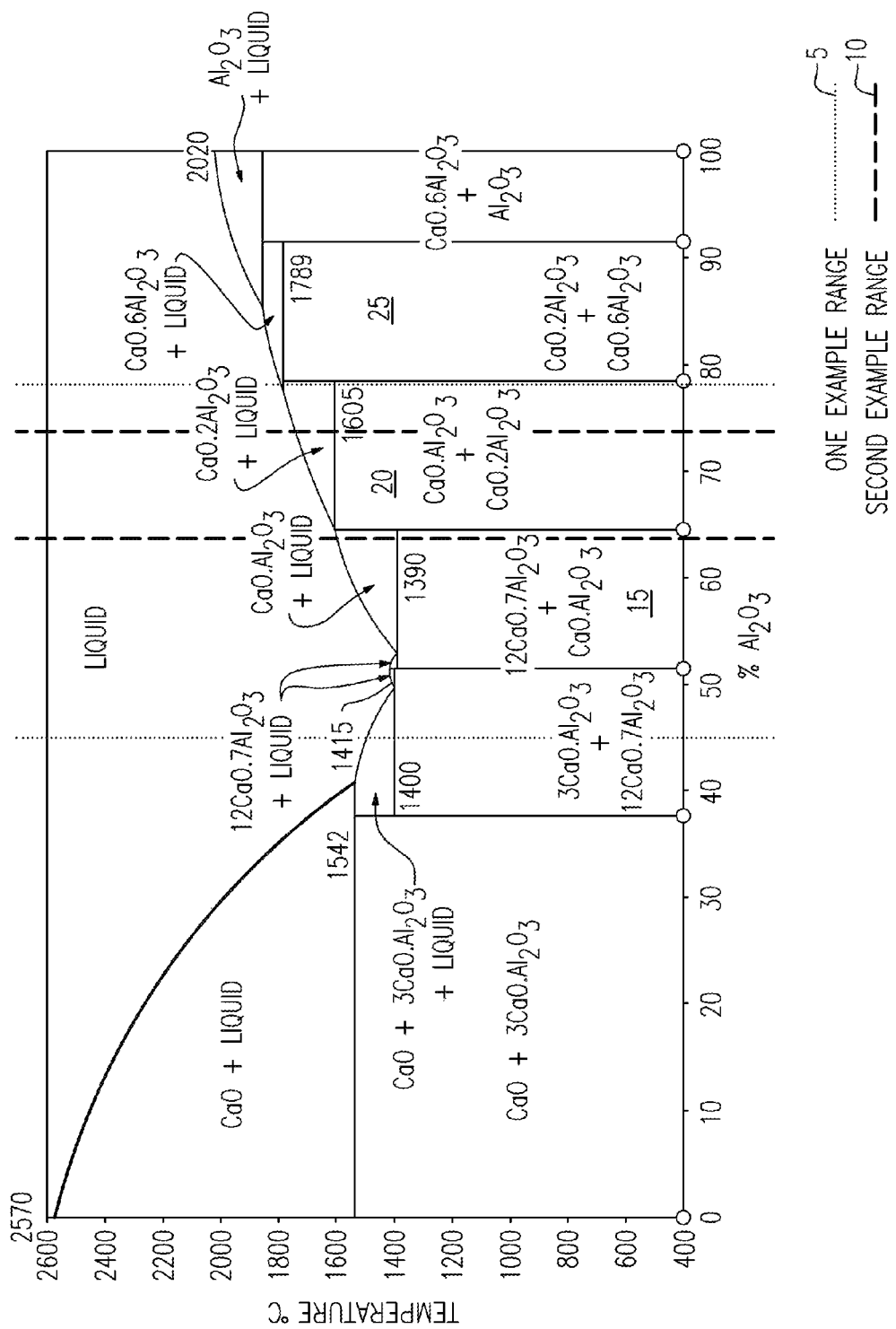
FIG. 1 is a diagram that depicts the percentage of aluminum oxide on the x axis and temperature on the y axis, showing various calcium oxide-aluminum oxide composition ranges for the calcium aluminate cements, and shows particular aluminum oxide percentages and temperature ranges for the compositions according to disclosed embodiments.
Figure 2:
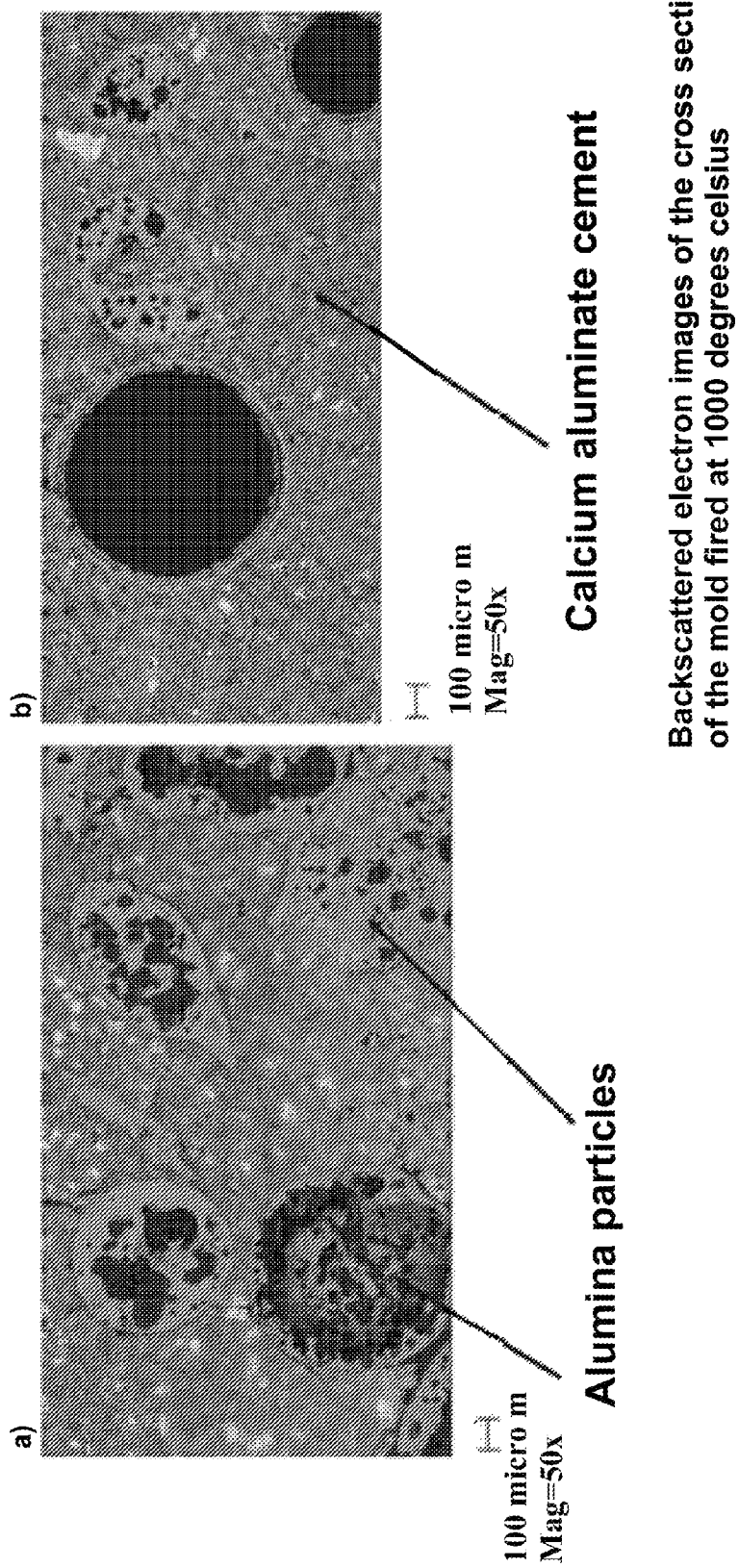
FIGS. 2a and 2b show one example of the mold microstructure after high temperature firing. The backscattered scanning electron microscope images of the cross section of the mold fired at 1000 degrees Celsius are shown, wherein FIG. 2a points to the alumina particles present and FIG. 2b points to the calcium aluminate cement.
Figure 3:
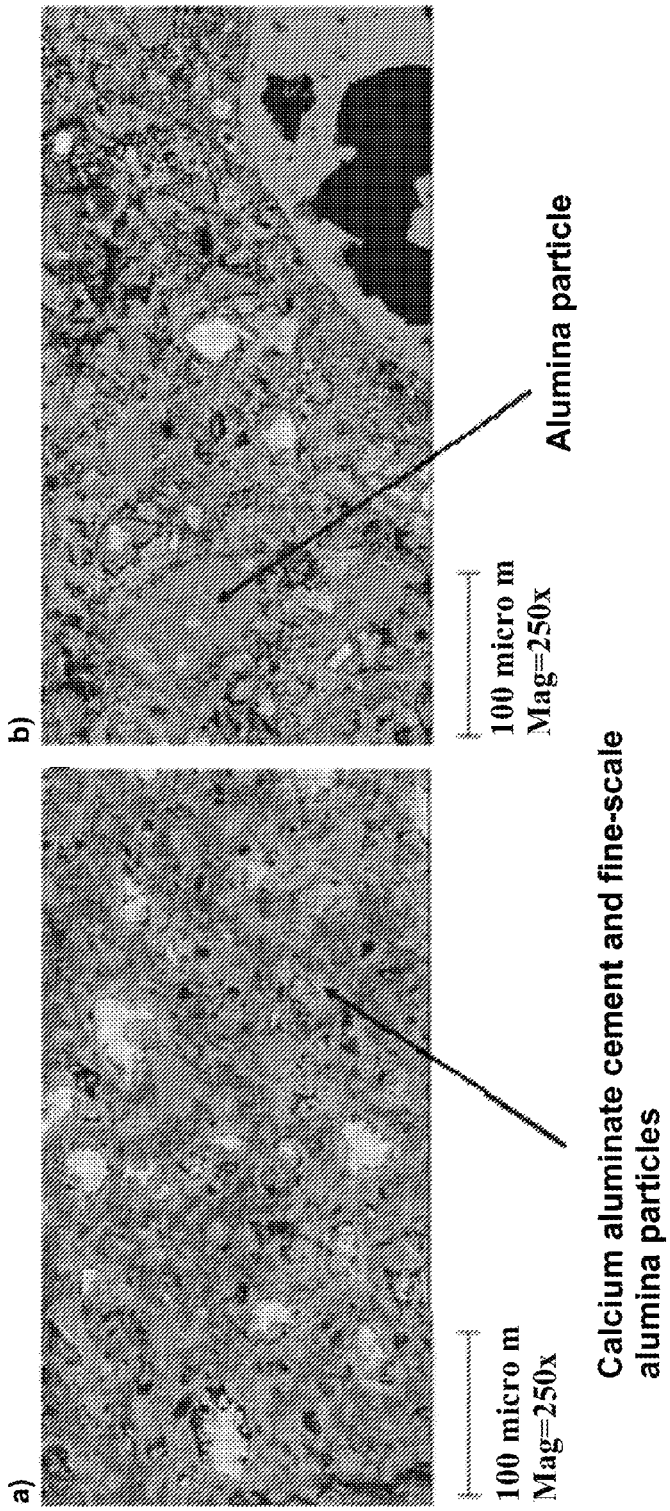
FIG. 3a and FIG. 3b show one example of the mold microstructure after high temperature firing. The backscattered scanning electron microscope images of the cross section of the mold fired at 1000 degrees Celsius are shown, wherein FIG. 3a points to calcium aluminate cement and fine-scale alumina particles present and FIG. 3b points to an alumina particle.
Figure 4:
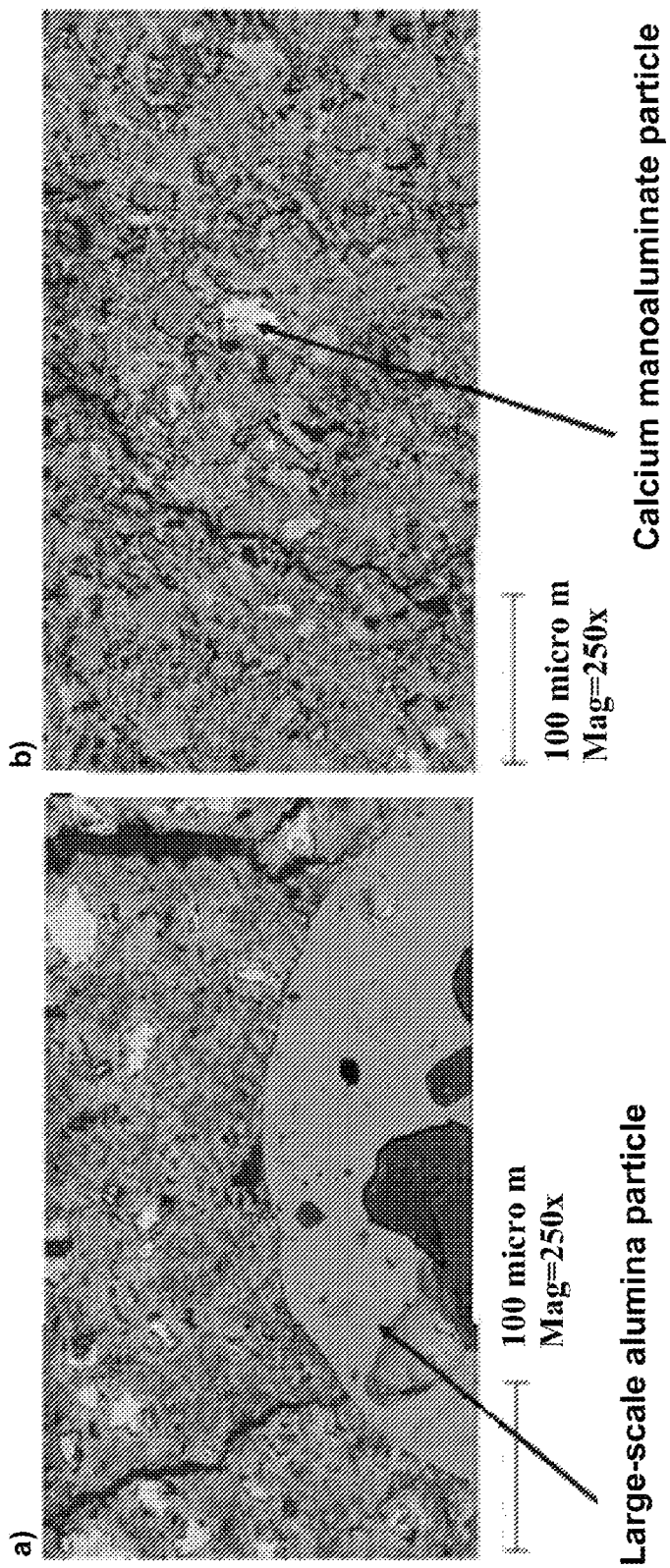
FIG. 4a and FIG. 4b show on example of the mold microstructure after high temperature firing. The backscattered scanning electron microscope images of the cross section of the mold fired at 1000 degrees Celsius are shown, wherein FIG. 4a points to a large scale alumina particle and FIG. 4b points to a calcium monoaluminate particle.
Figure 5:
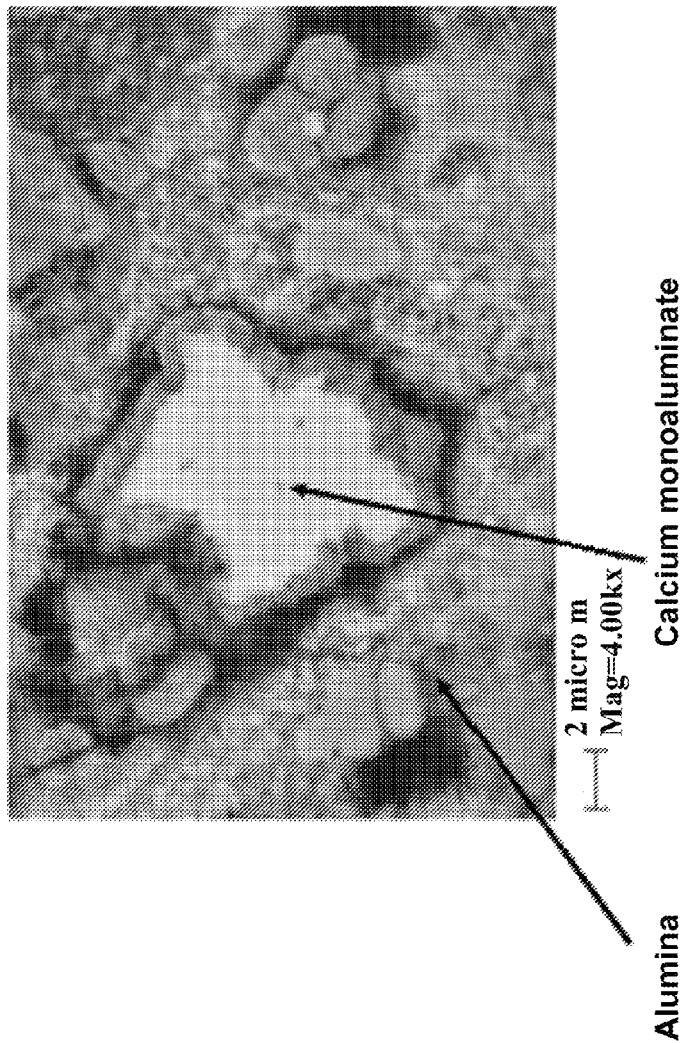
FIG. 5 shows one example of the mold microstructure after high temperature firing, showing alumina and calcium monoaluminate, wherein the calcium monoaluminate reacts with alumina to form calcium dialuminate, and wherein the mold in one example is fired to minimize mayenite content.
Figure 6:
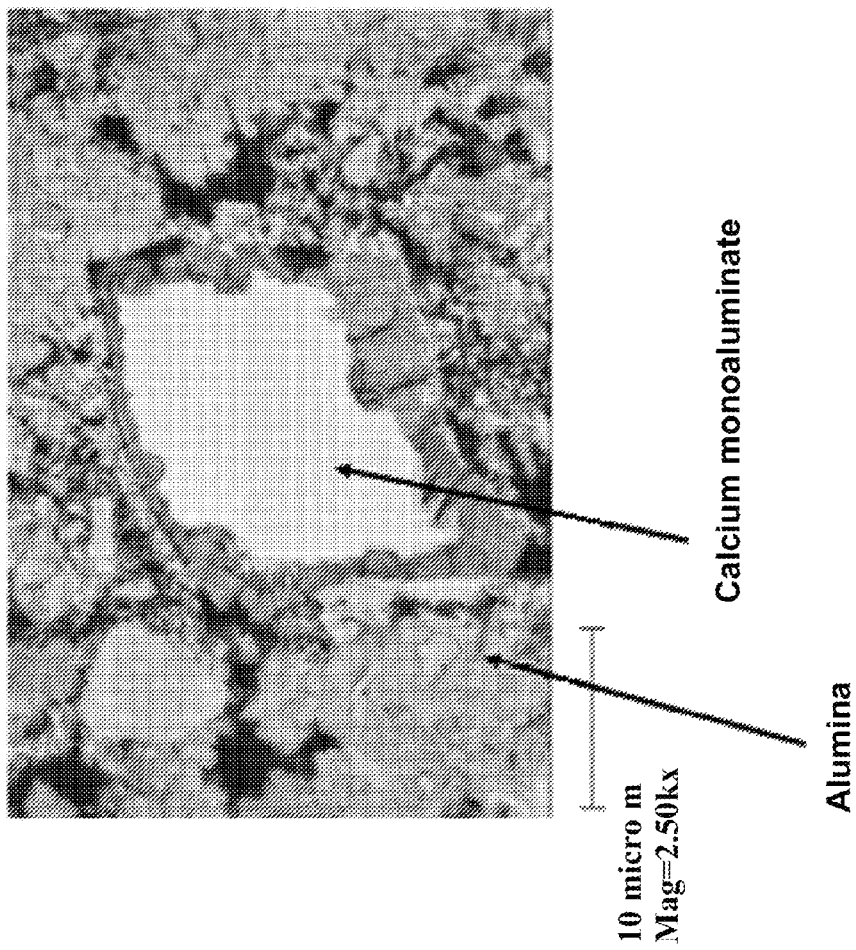
FIG. 6 shows one example of the mold microstructure after high temperature firing, showing alumina and calcium monoaluminate, wherein the calcium monoaluminate reacts with alumina to form calcium dialuminate, and wherein the mold is fired to minimize mayenite content.

Embodiments of the present disclosure provide a mold and a method of making titanium aluminide and titanium aluminide alloy castings of high structural integrity, by providing for easy detectability of inclusions, for example, surface and/or sub-surface inclusions, that may be present at and/or below the exterior surface of the casting. These inclusions can be generated from the molten metal, from the mold fabrication process, and/or from the casting process, for example, during investment casting. In one aspect, a surface zone may form during casting as a hard, brittle layer, known as the "alpha case" in the art, which may contain undesirable inclusions. The thickness of this layer is usually approximately 0.03 millimeters [mm].

The manufacture of titanium based airframe components by investment casting of titanium and its alloys in investment shell molds poses problems from the standpoint that the castings should be cast to "near-net-shape." That is, the components may be cast to substantially the final desired dimensions of the component, and require little or no final treatment or machining. For example, some castings may require only a chemical milling operation to remove any alpha case present on the casting. However, any sub-surface ceramic inclusions located below the alpha case in the casting are typically not removed by the chemical milling operation. These sub-surface inclusions are not visible upon visual inspection of the casting, even after chemical milling, and remain in the casting below the alpha case layer. These inclusions may be formed due to the reaction between the mold facecoat and any reactive metal in the molding medium, for example, reactive titanium aluminide.

The present disclosure provides a new approach for casting near-net-shape titanium and titanium aluminide components, such as, turbine blades or airfoils. Embodiments of the present disclosure provide compositions of matter for investment casting molds and casting methods that can provide improved titanium and titanium alloy components for example, for use in the aerospace industry. In some aspects, the mold composition provides a mold that may contain phases that provide improved mold strength during mold making and/or increased resistance to reaction with the casting metal during casting. The molds according to aspects of the disclosure may be capable of casting at high pressure, which is desirable for near-net-shape casting methods. A mold composition, for example, containing calcium aluminate cement and alumina particles, and preferred constituent phases, have been identified that provide castings with improved properties.

In one aspect, the constituent phases of the mold comprise calcium monoaluminate ($CaAl_2O_4$). The present inventors found calcium monoaluminate highly desirable for at least two reasons. First, it is understood by the inventors that calcium monoaluminate is believed to promote hydraulic bond formation between the cement particles during the initial stages of mold making, and this hydraulic bonding is believed to provide mold strength during mold construction. Second, it is understood by the inventors that calcium monoaluminate experiences a very low rate of reaction with titanium and titanium aluminide based alloys. In a certain embodiment, calcium monoaluminate is provided to the mold composition of the present disclosure, for example, the investment molds, in the form of calcium aluminate cement. In one aspect, the mold composition comprises a mixture of calcium aluminate cement and alumina, that is, aluminum oxide.

In one aspect of the disclosure, the mold composition provides minimum reaction with the alloy during casting, and the mold provides castings with the required component properties. External properties of the casting include features such as shape, geometry, and surface finish. Internal properties of the casting include mechanical properties, microstructure, defects (such as pores and inclusions) below a specified size and within allowable limits.

The mold composition of one aspect of the present disclosure provides for low-cost casting of titanium aluminide (TiAl) turbine blades, for example, TiAl low pressure turbine blades. The mold composition may provide the ability to cast near-net-shape parts that require less machining and/or treatment than parts made using conventional shell molds and gravity casting. As used herein, the expression "near-net-shape" implies that the initial production of an article is close to the final (net) shape of the article, reducing the need for further treatment, such as, extensive machining and surface finishing. As used herein, the term "turbine blade" refers to both steam turbine blades and gas turbine blades.

Accordingly, the present inventors address the challenges of producing a mold, for example, an investment mold, that does not react significantly with titanium and titanium aluminide alloys. In addition, according to some aspects of the disclosure, the strength and stability of the mold allow high pressure casting approaches, such as centrifugal casting. One of the technical advantages of aspects of the this disclosure is that, in one aspect, the disclosure may improve the structural integrity of net shape casting that can be generated, for example, from calcium aluminate cement and alumina investment molds. The higher strength, for example, higher fatigue strength, allows lighter components to be fabricated. In addition, components having higher fatigue strength can last longer, and thus have lower life-cycle costs.

Casting Mold Composition

Aspects of the present disclosure provide a composition of matter for investment casting molds that can provide improved components of titanium and titanium alloys. In one aspect of the present disclosure, calcium monoaluminate can be provided in the form of calcium aluminate cement. Calcium aluminate cement may be referred to as a "cement" or "binder." In certain embodiments, calcium aluminate cement is mixed with alumina particulates to provide a castable investment mold mix. The calcium aluminate cement may typically be greater than about 30% by volume in the castable mold mix. In certain embodiments, the calcium aluminate cement is between about 30% and about 60% by volume in the castable mold mix. The use of greater than 30% by volume of calcium aluminate cement in the castable mold mix (casting mold composition) is a feature of the present disclosure. The selection of the appropriate calcium aluminate cement chemistry and alumina formulation are factors in the performance of the mold. In one aspect, a sufficient amount of calcium oxide may be provided in the mold composition in order to minimize reaction with the titanium alloy.

In one aspect, the mold composition, for example, the investment mold composition, may comprise a multi-phase mixture of calcium aluminate cement and alumina particles. The calcium aluminate cement may function as a binder, for example, the calcium aluminate cement binder may provide the main skeletal structure of the mold structure. The calcium aluminate cement may comprise a continuous phase in the mold and provide strength during curing, and casting. The mold composition may consist of calcium aluminate cement and alumina, that is, calcium aluminate cement and alumina may comprise substantially the only components of the mold composition, with little or no other components. In one embodiment, the present disclosure comprises a titanium-containing article casting-mold composition comprising calcium aluminate. In another embodiment, the casting-mold composition further comprises oxide particles, for example, hollow oxide particles. According to aspects of the disclosure, the oxide particles may be aluminum oxide particles, magnesium oxide particles, calcium oxide particles, zirconium oxide particles, titanium oxide particles, and/or silica oxide particles, or combinations thereof.

The casting-mold composition can further include aluminum oxide, for example, in the form of hollow particles, that is, particles having a hollow core or a substantially hollow core substantially surrounded by an oxide. These hollow aluminum oxide particles may comprise about 99% of aluminum oxide and have about 0.5 millimeter [mm] or less in outside dimension, such as, width or diameter. In certain embodiments, the hollow oxide particles may comprise hollow alumina spheres. The hollow alumina spheres may be incorporated into the casting-mold composition, and the hollow spheres may have a range of geometries, such as, round particles, or irregular aggregates. In certain embodiments, the alumina may include both round particles and hollow spheres. In one aspect, these geometries were found to increase the fluidity of the investment mold mixture. The enhanced fluidity may typically improve the surface finish and fidelity or accuracy of the surface features of the final casting produced from the mold.

The aluminum oxide comprises particles ranging in outside dimension from about 10 microns to about 10,000 microns. In certain embodiments, the aluminum oxide comprises particles that are less than about 500 microns in outside dimension, for example, diameter or width. The aluminum oxide may comprise from about 0.5% by weight to about 80% by weight of the casting-mold composition. Alternatively, the aluminum oxide comprises from about 40% by weight to about 60% by weight of the casting-mold composition.

In one embodiment, the casting-mold composition further comprises calcium oxide. The calcium oxide may be greater than about 15% by weight and less than about 50% by weight of the casting-mold composition. The final mold typically may have a density of less than 2 grams/cubic centimeter and strength of greater than 500 pounds per square inch [psi]. In one embodiment, the calcium oxide is greater than about 30% by weight and less than about 50% by weight of the casting-mold composition. Alternatively, the calcium oxide is greater than about 25% by weight and less than about 35% by weight of the casting-mold composition.

In a specific embodiment, the casting-mold composition of the present disclosure comprises a calcium aluminate cement. The calcium aluminate cement includes at least three phases or components comprising calcium and aluminum: calcium monoaluminate ($CaAl_2O_4$), calcium dialuminate ($CaAl_4O_7$), and mayenite ($Ca_{12}Al_{14}O_{33}$). The volume fraction of calcium monoaluminate may range from 0.05 to 0.95; the volume fraction of calcium dialuminate may range from 0.05 to 0.80; and the volume fraction of mayenite may range from 0.01 to 0.30. In another example, the volume fraction of calcium monoaluminate comprises a volume fraction of about 0.1 to about 0.8; the calcium dialuminate comprises a volume fraction of about 0.1 to about 0.6; and the mayenite comprises a volume fraction of about 0.01 to about 0.2. The volume fraction of calcium monoaluminate in the calcium aluminate cement may be more than about 0.5, and the volume fraction of mayenite in the calcium aluminate cement may be less than about 0.15. In another embodiment, the calcium aluminate cement is more than 30% by weight of the casting-mold composition.

In one embodiment, the calcium aluminate cement has a particle size of about 50 microns or less. A particle size of less than 50 microns is preferred for three reasons: first, the fine particle size is believed to promote the formation of hydraulic bonds during mold mixing and curing; second, the fine particle size is understood to promote inter-particle sintering during firing, and this can increase the mold strength; and third, the fine particle size is believed to improve the surface finish of the molded article. The calcium aluminate cement may be provided as powder, and can be used either in its intrinsic powder form, or in an agglomerated form, such as, as spray dried agglomerates. The calcium aluminate cement can also be preblended with fine-scale (for, example, less than 10 micron in size) alumina. The fine-scale alumina is believed to provide an increase in strength due to sintering during high-temperature firing. In certain instances, larger-scale alumina (that is, greater than 10 micron in size) may also be added with or without the fine-scale alumina.

Calcium Aluminate Cement Composition

The calcium aluminate cement used in aspects of the disclosure typically comprises three phases or components of calcium and aluminum: calcium monoaluminate ($CaAl_2O_4$), calcium dialuminate ($CaAl_4O_7$), and mayenite ($Ca_{12}Al_{14}O_{33}$). Calcium mono-aluminate is a hydraulic mineral present in calcium alumina cement. Calcium monoaluminate's hydration contributes to the high early strength of the investment mold. Mayenite is desirable in the cement because it provides strength during the early stages of mold curing due to the fast formation of hydraulic bonds. The mayenite is, however, typically removed during heat treatment of the mold prior to casting.

In one aspect, the initial calcium aluminate cement formulation is typically not at thermodynamic equilibrium after firing in the cement manufacturing kiln. However, after mold making and high-temperature firing, the mold composition moves towards a thermodynamically stable configuration, and this stability is advantageous for the subsequent casting process. In one embodiment, the volume fraction of calcium monoaluminate in the cement is greater than 0.5, and volume fraction of mayenite is less than 0.15. The mayenite is incorporated in the mold because it is a fast setting calcium aluminate and it is believed to provide the cement with strength during the early stages of curing. Curing may be performed at low temperatures, for example, temperatures between 15 degrees Celsius and 40 degrees Celsius because the fugitive wax pattern is temperature sensitive and loses its shape and properties on thermal exposure above about 35 degrees C. It is preferred to cure the mold at temperatures below 30 degrees C.

The calcium aluminate cement may typically be produced by mixing high purity alumina with high purity calcium oxide or calcium carbonate; the mixture of compounds is typically heated to a high temperature, for example, temperatures between 1000 and 1500 degrees C. in a furnace or kiln and allowed to react.

The resulting product, known in the art as cement "clinker," that is produced in the kiln is then crushed, ground, and sieved to produce a calcium aluminate cement of the preferred particle size. Further, the calcium aluminate cement is designed and processed to have a minimum quantity of impurities, such as, minimum amounts of silica, sodium and other alkali, and iron oxide. In one aspect, the target level for the calcium aluminate cement is that the sum of the $Na_2O$, $SiO_2$, $Fe_2O_3$, and $TiO_2$ is less than about 2 weight percent. In one embodiment, the sum of the $Na_2O$, $SiO_2$, $Fe_2O_3$, and $TiO_2$ is less than about 0.05 weight percent.

In one aspect of the disclosure, a calcium aluminate cement with bulk alumina concentrations over 35% weight in alumina ($Al_2O_3$) and less than 65% weight calcium oxide is provided. The maximum alumina concentration of the cement may be about 85% (for example, about 15% CaO). In one embodiment, the calcium aluminate cement is of high purity and contains up to 70% alumina. The volume fraction of calcium monoaluminate may be maximized in the fired mold prior to casting. A minimum amount of calcium oxide may be required to minimize reaction between the casting alloy and the mold. If there is more than 50% calcium oxide in the cement, this can lead to phases such as mayenite and tricalcium aluminate, and these do not perform as well as the calcium monoaluminate during casting. The preferred range for calcium oxide is less than about 50% and greater than about 15% by weight.

As noted above, the three phases in the calcium aluminate cement/binder in the mold are calcium monoaluminate ($CaAl_2O_4$), calcium dialuminate ($CaAl_4O_7$), and mayenite ($Ca_{12}Al_{14}O_{33}$). The calcium monoaluminate in the cement/binder has three advantages over other calcium aluminate phases: 1) The calcium monoaluminate is incorporated in the mold because it has a fast setting response (although not as fast as mayenite) and it is believed to provide the mold with strength during the early stages of curing. The rapid generation of mold strength provides dimensional stability of the casting mold, and this feature improves the dimensional consistency of the final cast component. 2) The calcium monoaluminate is chemically very stable with regard to the titanium and titanium aluminide alloys that are being cast. The calcium monoaluminate is preferred relative to the calcium dialuminate, and other calcium aluminate phases with higher alumina activity; these phases are more reactive with titanium and titanium aluminide alloys that are being cast. 3) The calcium monoaluminate and calcium dialuminate are low expansion phases and are understood to prevent the formation of high levels of stress in the mold during curing, dewaxing, and subsequent casting. The thermal expansion behavior of calcium monoaluminate is a close match with alumina.

Casting Mold Composition with Improved Detectability

There is a small difference in the X-ray density of the mold materials (calcium aluminate cement and alumina) and titanium, and inclusions that originate from the mold are therefore difficult to detect. In order to address this limitation, species can be added to the ceramic investment mix to enhance X-ray detectability of inclusions.

One aspect of the disclosure is a mold composition for casting a titanium-containing article, comprising: a calcium aluminate cement comprising calcium monoaluminate, calcium dialuminate, and mayenite; and an X-ray or Neutron-ray detectable element. Another aspect of the present disclosure is a titanium-containing article casting-mold composition, comprising: calcium aluminate; and an X-ray or Neutron-ray detectable element. In one embodiment, the calcium aluminate cement forms an intrinsic facecoat of less than about 100 microns when the mold composition forms a mold. In one embodiment, the X-ray or Neutron-ray detectable elements are mixed within the mold. In another embodiment, the X-ray or Neutron-ray detectable elements are mixed within the mold and become part of the intrinsic facecoat.

There are several different methods that X-ray or Neutron-ray detectable elements can be mixed with the mold mix. For example, the element can be added as a liquid such as a nitrate at any stage of the mold mixing process. The element can also be added as an oxide, as described herein. In one embodiment, the element is combined as an oxide with alumina in a fused form, such as an erbium aluminum garnet, or dysprosium aluminum garnet, prior to generating the mold mix. It will be understood by someone skilled in the art of ceramic mold making that different approaches can be employed to introduce the X-ray or Neutron-ray detectable elements into the mold. In one embodiment, the mold composition does not have an extrinsic facecoat.

The mold composition may further comprise oxide particles. The oxide particles comprise particles of at least one of aluminum oxide, magnesium oxide, calcium oxide, zirconium oxide, and titanium oxide. In a specific embodiment, the oxide particles are aluminum oxide particles. The titanium-containing cast article can be an engine, a turbine, or a turbine blade.

Since there is only a small difference between the X-ray density of the mold materials (calcium aluminate cement and alumina) and the X-ray density of titanium, inclusions that originate from the mold are difficult to detect. Here, the inventors added certain X-ray detectable elements to their investment mix to enhance the detectability of the sub-surface inclusions. Accordingly, one aspect of the present disclosure is a method for detecting sub-surface ceramic inclusions in a titanium or titanium alloy casting, comprising: combining calcium aluminate, an element more radiographically dense than the calcium aluminate, and a liquid to form a slurry; forming a mold having the calcium aluminate and the radiographically dense element from the slurry; introducing a titanium aluminide-containing metal to the radiographically dense element-bearing mold; solidifying said titanium aluminide-containing metal to form an article in the mold; removing the solidified titanium aluminide-containing metal article from said mold; subjecting the solidified titanium aluminide-containing article to radiographic inspection to provide a radiograph; and examining said radiograph for the presence of the radiographically dense element on or in the article. In one embodiment, the method comprises minimizing the presence of mold material inclusions in titanium aluminide-containing cast articles.

The combining step further comprises combining oxide particles with the slurry. A liquid, such as water, for example, deionized water, may be added to the slurry to adjust slurry viscosity. Any viscosity measuring protocol or instrument may be used. Typically, viscosity is adjusted to be within 8-20 seconds, preferably, 9-12 seconds, for the cement slurry mixing as determined by using the Zahn cup viscosity measurement technique; this technique is well known to those skilled in the art. The amount of water present in the slurry is limited so as not to diminish the green or fired strength of the shell mold. In certain embodiments, the radiographically dense element is more radiographically dense than the oxide particles, for example, the radiographically dense element is more radiographically dense than calcium oxide. In certain embodiments, the oxide particles comprise hollow oxide particles, for example, hollow aluminum oxide particles.

One of the advantages of the present disclosure is that castings can be produced that provide enhanced detectability of any surface and/or sub-surface inclusions on, proximate, and/or below the surface of the casting that are typically not detectable by visual inspection. For example, inclusions that may be located below an alpha case layer of a titanium based casting and that are not removed by a post-cast chemical milling operation or other surface treatments may be detected by aspects of the disclosure. Moreover, conventional chemical milling regimes can still be used to remove the alpha case from the casting because practicing the disclosure does not promote further formation of alpha case on titanium based castings.

One aspect of the present disclosure provides a composition of matter for casting molds, for example, investment casting molds, that can provide improved X-ray or Neutron-ray inspectability for inclusions that can undesirably occur in the casting, for example, from the casting molding. In one embodiment, this is achieved by the addition of an element more radiographically dense than the casting mold composition, for example, more radiographically dense than calcium aluminate. In one aspect, the present disclosure is a mold composition for casting titanium-containing articles, comprising: calcium aluminate; and an X-ray or Neutron-ray detectable element. The titanium-containing cast article can be a titanium aluminide engine component, a titanium aluminide turbine, or a titanium aluminide turbine blade. In one embodiment, the X-ray or Neutron-ray detectable element that can be used include at least one of ytterbium, hafnium, gadolinium, tungsten, thorium, uranium, yttrium, dysprosium, erbium, cerium, and compositions thereof. These elements are used in some instances because they are more radiographically dense than the calcium aluminate.

One aspect of the present disclosure is a mold composition comprising: calcium aluminate cement comprising calcium monoaluminate, calcium dialuminate, and mayenite; and at least one element more radiographically dense than the calcium aluminate cement. Another aspect of the present disclosure is a mold composition comprising calcium aluminate and at least one element more radiographically dense than the calcium aluminate. Erbium, dysprosium, and/or gadolinium-bearing calcium aluminate cement and alumina investment mixes have the advantage of the relatively high X-ray detectability of erbium, dysprosium, and gadolinium compared to other elements. An additional advantage is that erbium, dysprosium, and gadolinium are also resistant to reaction with molten titanium and titanium alloys during casting. The erbium, dysprosium, and/or gadolinium-bearing investment mix are not radioactive compared to $ThO_2$ and other radioactive bearing mold compositions and thus are preferred in some embodiments.

The mold formulation may not form an extrinsic facecoat, such as yttrium, when formed into a mold, but the formulation may be a homologous two-phase composition of calcium aluminate and alumina. During investment mixing, pouring and curing, the mold forms an intrinsic facecoat of calcium aluminate in the mold. According to an aspect of the disclosure, the intrinsic facecoat (typically less than 100 microns thick) of calcium aluminate in the mold also contains particles of radiographically dense elements, for example, erbium and/or dysprosium and/or gadolinium mixed within the mold material. The erbium, dysprosium, gadolinium bearing additions to the investment mix are used for the molds for making titanium aluminide and titanium aluminide alloy castings because erbium, dysprosium, and gadolinium exhibit a greater X-ray density than that of other ceramic components. Some of the radiographically dense elements, for example, erbium, dysprosium, and gadolinium also exhibit acceptable resistance to reaction with molten titanium aluminide and titanium aluminide alloys during the casting operation.

The Mold, Casting Methods and Detecting Sub-Surface Inclusions

An investment mold is formed by formulating the investment mix of the ceramic components, and pouring the mix into a vessel that contains a fugitive pattern. The investment mold formed on the pattern is allowed to cure thoroughly to form a so-called "green mold." Typically, curing of the green mold is performed for times from 1 hour to 48 hours. Subsequently, the fugitive pattern is selectively removed from the green mold by melting, dissolution, ignition, or other known pattern removal technique. Typical methods for wax pattern removal include oven dewax (less than 150 degrees C.), furnace dewax (greater than 150 degrees C.), steam autoclave dewax, and microwave dewaxing.

For casting titanium alloys, and titanium aluminide and its alloys, the green mold then is fired at a temperature above 600 degrees C., preferably 700 to 1400 degrees C., for a time period in excess of 1 hour, preferably 2 to 6 hours, to develop mold strength for casting and to remove any undesirable residual impurities in the mold, such as metallic species (Fe, Ni, Cr), and carbon-containing species. The atmosphere of firing the mold is typically ambient air, although inert gas or a reducing gas atmosphere can be used.

The firing process also removes the water from the mold and converts the mayenite to calcium aluminate. Another purpose of the mold firing procedure is to minimize any free silica that remains in the mold prior to casting. Other purposes are to remove the water, increase the high temperature strength, and increase the amount of calcium monoaluminate and calcium dialuminate.

The mold is heated from room temperature to the final firing temperature, specifically the thermal history and the humidity profile are controlled. The heating rate to the firing temperature, and the cooling rate after firing are typically regulated or controlled. If the mold is heated too quickly, it can crack internally or externally, or both; mold cracking prior to casting is highly undesirable. In addition, if the mold is heated too quickly, the internal surface of the mold can crack and spall off. This can lead to undesirable inclusions in the final casting, and poor surface finish, even if there are no inclusions. Similarly, if the mold is cooled too quickly after reaching the maximum temperature, the mold can also crack internally or externally, or both.

The mold composition described in the present disclosure is particularly suitable for titanium and titanium aluminide alloys. The mold composition after firing and before casting can influence the mold properties, particularly with regard to the constituent phases. In one embodiment, for casting purposes, a high volume fraction of calcium monoaluminate in the mold is preferred, for example, a volume fraction of 0.3 to 0.8. In addition, for casting purposes, it is desirable to minimize the volume fraction of the mayenite, for example, using a volume fraction of 0.01 to 0.2, because mayenite is water sensitive and it can provide problems with water release and gas generation during casting. After firing, the mold can also contain small volume fractions of aluminosilicates and calcium aluminosilicates. The sum of the volume fraction of aluminosilicates and calcium aluminosilicates may typically be kept to less than 5% in order to minimize reaction of the mold with the casting.

In certain embodiments, the casting-mold composition of the present disclosure comprises an investment casting-mold composition. The investment casting-mold composition comprises a near-net-shape, titanium-containing metal, investment casting mold composition. In one embodiment, the investment casting-mold composition comprises an investment casting-mold composition for casting near-net-shape titanium aluminide articles. The near-net-shape titanium aluminide articles comprise, for example, near-net-shape titanium aluminide turbine blades.

The selection of the correct calcium aluminate cement chemistry and alumina formulation are factors in the performance of the mold during casting. In terms of the calcium aluminate cement, it may be necessary to minimize the amount of free calcium oxide in order to minimize reaction with the titanium alloy. If the calcium oxide concentration in the cement is less than 15% by weight, the alloy reacts with the mold because the alumina concentration is too high, and the reaction generates undesirable oxygen concentration levels in the casting, gas bubbles, and a poor surface finish in the cast component. If the calcium oxide concentration in the cement is greater than 50% by weight, the mold can be sensitive to pick up of water and carbon dioxide from the environment. As such, the calcium oxide concentration in the investment mold may typically be kept below 50%. In one embodiment, the calcium oxide concentration is between 15% and 40% by weight. Alternatively, the calcium oxide concentration can be between 25% and 35% by weight.

Carbon dioxide can lead to formation of calcium carbonate in the mold during processing and prior to casting, and calcium carbonate is unstable during the casting operation. Thus, the water and carbon dioxide in the mold can lead to poor casting quality. If the adsorbed water level is too high, for example, greater than 0.05 weight percent, when the molten metal enters the mold during casting, the water is released and it can react with the alloy. This leads to poor surface finish, gas bubbles in the casting, high oxygen concentration, and poor mechanical properties. Similarly, if the carbon dioxide level is too high, calcium carbonate can form in the mold and when the molten metal enters the mold during casting, the calcium carbonate can decompose generating carbon dioxide, which can react with the alloy. The resulting calcium carbonate is less than 1 percent in weight of the mold.

Prior to casting a molten metal or alloy, the investment mold typically is preheated to a mold casting temperature that is dependent on the particular component geometry or alloy to be cast. For example, a typical mold preheat temperature is 600 degrees C. Typically, the mold temperature range is 450 degrees C. to 1200 degrees C.; the preferred temperature range is 450 degrees C. to 750 degrees C., and in certain cases it is 500 degrees C. to 650 degrees C.

According to one aspect, the molten metal or alloy is poured into the mold using conventional techniques which can include gravity, countergravity, pressure, centrifugal, and other casting techniques known to those skilled in the art. Vacuum or an inert gas atmospheres can be used. For complex shaped thin wall geometries, techniques that use high pressure are preferred. After the solidified titanium aluminide or alloy casting is cooled typically to less than 650 degrees, for example, to room temperature, it is removed from the mold and finished using conventional techniques, such as, grit blasting, water jet blasting, and polishing.

One aspect of the present disclosure is a method for detecting sub-surface ceramic inclusions in a titanium or titanium alloy casting, comprising: combining calcium aluminate, at least one element more radiographically dense than the calcium aluminate, and a liquid to form a slurry; forming a mold having the calcium aluminate and the radiographically dense element from the slurry; introducing a titanium aluminide-containing metal to the radiographically dense element-bearing mold; solidifying said titanium aluminide-containing metal to form an article in the mold; removing the solidified titanium aluminide-containing metal article from said mold; subjecting the solidified titanium aluminide-containing article to radiographic inspection to provide a radiograph; and examining said radiograph for the presence of the radiographically dense element on or in the article. In one embodiment, the method comprises minimizing the presence of mold material inclusions in titanium aluminide-containing cast articles.

Between removing said fugitive pattern from the mold and preheating the mold to a mold casting temperature, the mold is first heated to a temperature of about 450 degrees C. to about 900 degrees C., and then cooled to room temperature. In one embodiment, the curing step is conducted at temperatures below about 30 degrees C. for between one hour to 48 hours. The removing of the fugitive pattern includes the step of melting, dissolution, ignition, oven dewaxing, furnace dewaxing, steam autoclave dewaxing, or microwave dewaxing. In one embodiment, after removing of the titanium or titanium alloy from the mold, the casting may be finished with grit blasting, water jet blasting, or polishing. After the solidified casting is removed from the mold, it is inspected by X-ray or Neutron radiography.

For the present disclosure, the solidified casting is subjected to surface inspection and X-ray radiography after casting and finishing to detect any sub-surface inclusion particles at any location within the casting. X-ray radiography is employed to find inclusions that are not detectable by visual inspection of the exterior surface of the casting. The titanium aluminide casting is subjected to X-ray radiography (film or digital) using conventional X-ray equipment to provide an X-ray radiograph that then is inspected or analyzed to determine if any sub-surface inclusions are present within the titanium aluminide casting.

The sub-surface inclusions can originate from the investment mold facecoat or mold facecoat as a result of erosion of the mold during mold filling, reaction between the reactive molten metal and the mold facecoat, and/or mechanical spallation as a result of thermal shock of the mold. When a sub-surface inclusion or inclusions are found using the X-ray methods, the casting may be subjected to grinding and weld repair operations to remove and replace sufficient material to remove the objectionable inclusions; alternatively the casting may be scrapped if the inclusion(s) is/are larger than a specified size for the required mechanical integrity of the casting.

The solidified casting is typically subjected to surface inspection and X-ray radiography after casting and finishing to detect any ceramic inclusion particles, for example, sub-surface inclusion particles, at any location within the casting. Erbium, dysprosium, and gadolinium bearing calcium aluminate cement and alumina investment mixes are used. The erbium bearing calcium aluminate cement and alumina investment mix can be selected from fused, calcined or sintered erbia (erbium oxide) powder in the fused form, or other form. Fused erbia powder is preferred as the erbia slurry component since it is more dense and resistant to chemical reaction with a titanium aluminide or titanium aluminide alloy melt than calcined or sintered erbia powder. A fused erbia powder can be added to the investment mold mix during mixing, at any stage. In one embodiment, the fused erbia powder is added with the calcium aluminate cement. A fused erbia powder particularly useful in practicing the disclosure is available as Auercoat 4/3 from Treibacher Auermet GmbH, A-9330 Treibach-Althofen, Austria, in the powder particle size of −325 mesh (less than 44 microns). A calcined erbia powder useful in practicing the disclosure is available as Auercoat 4/4 also from Treibacher Auermet GmbH in the particle size of −325 mesh (less than 44 microns). The mesh size refers to the U.S. Standard Screen System.

In one embodiment, the method further comprises the step of removing the radiographically dense element from the article. This removing of the radiographically dense element from the article can be achieved by one or more steps of machining, grinding, polishing, or welding. Chemical milling can also be used to remove the radiographically dense element from the article.

Since there is a risk of sub-surface inclusions becoming entrained in the cast component and thereby reducing the strength and load-bearing capability of the final casting, the present disclosure is directed to the detection and elimination of these sub-surface inclusions from the castings, so as to maximize the mechanical properties and the performance of the castings. The present disclosure provides methods for improving the structural integrity of castings by increasing the probability of detecting inclusions that can be generated from calcium aluminate cement and alumina investment molds during casting of titanium aluminide.

The present disclosure also allows the detection of smaller inclusions because of the greater X-ray contrast. The greater probability of detection of inclusions and the greater ability to detect smaller inclusions with the modern digital X-rays methods improve the strength and the fatigue strength of castings of titanium alloys and titanium aluminide alloys.

The mold compositions described provide a small amount of a material having a high Neutron absorption cross section. In one aspect, a Neutron radiograph is prepared of the cast article. Since the titanium alloy cast article may be substantially transparent to neutrons, the mold material will typically show up distinctly in the resulting Neutron radiograph. In one aspect, it is believed that Neutron exposure results in "neutron activation" of the radiographically dense element. Neutron activation involves the interaction of the Neutron radiation with the radiographically dense element of the casting to effect the formation of radioactive isotopes of the radiographically dense elements of the mold composition. The radioactive isotopes may then be detectable by conventional radioactive detecting devices to count any radiographically dense element isotopes present in the cast article.

A thermal Neutron beam can be obtained from a number of sources, including a nuclear reactor, a subcritical assembly, a radioactive Neutron source, or an accelerator. Images produced by N-ray can be recorded on a film, such as with X-ray.

This is accomplished generally by placing a part to be imaged in a Neutron beam, and then recording the image on a film for each angle at which an image is desired. N-ray images can also be taken in real time with modern digital detection equipment.

N-ray uses neutrons as a penetrating radiation for imaging inclusions. All energies of neutrons, e.g., fast, epithermal, thermal and cold neutrons, can be used for N-ray imaging. N-ray imaging is a process whereby radiation beam intensity modulation by an object is used to identify inclusions and defects. The components required for N-ray imaging include a source of fast neutrons, a moderator, a gamma filter, a collimator, a conversion screen, a film image recorder or other imaging system, a cassette, and adequate biological shielding and interlock systems.

In one aspect, the presently taught method may be used in the titanium aluminide castings when there is an addition to the mold material that is a strong absorber of neutrons. The Neutron absorbing additives are suitable because they have the desired high Neutron absorption cross section. Since generally Neutron radiographs are produced using neutrons having thermal or resonance energy levels, it is generally preferred that the Neutron absorbing material have a high absorption cross section for thermal neutrons. Example materials having high thermal Neutron absorption cross sections that are compatible with the titanium aluminide mold of the present disclosure include erbium, dysprosium, gadolinium, and mixtures thereof.

In general, the higher the Neutron absorption cross section of the additive, the smaller the quantity required to give the desired imaging characteristics. Generally, less than 10 weight percent is used. For example, the X-ray or Neutron-ray detectable component is in the range of about 0.5 to about 6 weight percent in the mold composition. Good results can be obtained with erbium, dysprosium, or gadolinium oxide in the range of about 1 to about 4 weight percent of the core material. Gadolinium has a very high Neutron absorption cross section and produces excellent images with small amounts in the mold. In one embodiment, solutions used to enhance N-ray and X-ray contrast comprise nitrate, halide, sulfate, perchlorate salts of the elements for N-ray and X-ray enhancement.

In one aspect, the selection of suitable mold additions for X-ray contrast enhancement and detection depends upon the difference between the density of the imaging agent and that of the titanium alloy casting. The selection of suitable mold additions for N-ray imaging of inclusions is determined by the linear attenuation coefficient or the thermal Neutron cross section of the imaging addition relative to that of the cast titanium part, and throughout the whole cross section of the casting.

In one aspect of the present disclosure, the inventors selected N-ray and X-ray contrast enhancing elements to add to the calcium aluminate investment mold based on factors, including: the stability of the oxide of the element against the mold metal (low reaction rate), the x-ray density in comparison with titanium, and the N-ray moderation in comparison with titanium, and availability/cost. With these criteria in mind, three species were identified: erbia, dysprosia, and gadolinia. Other contrast enhancing elements such as, neodymium, samarium, europium, holmium, ytterbium, lutetium were considered based on the above criteria, however, were not thought to provide the same results in this application as when gadolinium, erbium and dysprosium are used. In one embodiment, gadolinia, erbia and dysprosia are preferred for detecting inclusions that can come from calcium aluminate molds in casting titanium or titanium alloy.

With respect to X-ray detection of inclusions, the primary factors that effect detectability include (1) the difference between the density of the titanium alloy in comparison with the density of the inclusion, (2) the size, thickness, shape and orientation of the inclusion, and (3) the thickness of the cross section of the cast titanium alloy component. If the difference between the density of the cast material and the inclusion is small (such as less than about 0.5 g/cc), there may not be sufficient image contrast to detect the inclusion by X-ray. In these circumstances, N-ray is employed, provided the appropriate element is added for N-ray contrast enhancement.

In one aspect of the present disclosure, the selection of suitable imaging agents for X-ray detection depends upon the difference between the density of the imaging agent and that of the metal or alloy of the casting. In one example, the selection of suitable imaging agents for N-ray imaging of inclusions is determined by the linear attenuation coefficient or the Neutron absorption cross section of the material being used as an imaging agent relative to that of the metal or alloy being cast. The difference between the linear attenuation coefficient or the Neutron absorption cross section of the mold and that of the casting needs to be sufficient, so that any mold inclusions can be imaged throughout the cross section of the article.

Gadolinium is a preferred addition to the mold for imaging using N-ray detection of inclusions in titanium or titanium alloy castings. Gadolinium has a very high Neutron absorption cross section. Specifically, the Neutron absorption cross section of gadolinium is 259,000 barns, whereas the Neutron absorption cross section of titanium is about 6.1 barns. The Neutron absorption cross section of other elements include, dysprosium (2840 barns), erbium (659 barns), ettrium (1.3 barns), calcium (0.4 barns), aluminum (0.2 barns). As such, the N-ray imaging capability of calcium- and aluminum-containing inclusions, for example, is very low. (for additional information, see the National Institute of Standards and Technology Center for Neutron Research website). Therefore, the selection of the element is a feature of the disclosure, and isotopes of the selected elements may be used.

In one aspect, the addition of gadolinium or dysprosium, or erbium can substantially enhance the Neutron absorption capability with respect to titanium, and therefore the inclusion imaging contrast capability during N-ray is substantially enhanced. Gadolinium isotope 157 is believed to have a thermal Neutron absorption cross section of 259,000 barns. The difference between the Neutron absorption cross section of titanium or titanium alloys makes gadolinium particularly suitable for N-ray imaging. For metals and/or alloys other than titanium, gadolinium is also a preferred imaging agent, primarily because of the relatively large Neutron absorption cross of gadolinium.

One of the technical advantages of aspects of the disclosure is that it improves the structural integrity of castings of a titanium-containing article by allowing for improved detection of inclusions that can be generated from calcium aluminate cement and alumina investment mixes. The disclosure also allows the detection of smaller inclusions because of the greater X-ray contrast. The greater probability of detection of inclusions and the greater ability to detect smaller inclusions with the most modern digital X-rays methods improve the strength and the fatigue strength of castings of titanium alloys and titanium aluminide alloys. The higher strength allows lighter components, and the higher fatigue strength provides for components with longer lives, and thus lower life-cycle costs. In one embodiment, the component comprises a titanium aluminide turbine blade.

Examples

The disclosure, having been generally described, may be more readily understood by reference to the following examples, which are included merely for purposes of illustration of certain aspects and embodiments of the present disclosure, and are not intended to limit the disclosure in any way.

The Investment Mold Composition and Formulation

A calcium aluminate cement was mixed with alumina to generate an investment mold mix, and a range of investment mold chemistries were tested. The investment mixture consisted of calcium aluminate cement with 70% alumina and 30% calcia, alumina particles, water, and colloidal silica.

In a first example, a typical slurry mixture for making an investment mold consisted of 3000 grams [g] of the calcium aluminate cement, (comprising approximately 10% by weight of mayenite, approximately 70% by weight of calcium monoaluminate, and approximately 20% by weight of calcium dialuminate), 1500 g of calcined alumina particles with a size of less than 10 microns, 2450 g of high-purity calcined alumina particles of a size range from 0.5-1 mm diameter, 1650 g of deionized water, and 150 g of colloidal silica.

Typical high-purity calcined alumina particles types include fused, tabular, and levigated alumina. Typical suitable colloidal silicas include Remet LP30, Remet SP30, Nalco 1030, Ludox. The produced mold was used for casting titanium aluminide-containing articles such as turbine blades with a good surface finish. The roughness (Ra) value was less than 100 microinches, and with an oxygen content of less than 2000 parts per million [ppm]. This formulation produced a mold that was approximately 120 mm diameter and 400 mm long. This formulation produced a mold that had a density of less than 2 grams per cubic centimeter.

The mold mix was prepared by mixing the calcium aluminate cement, water, and colloidal silica in a container. A high-shear form mixing was used. If not mixed thoroughly, the cement can gel. When the cement was in full suspension in the mixture, the fine-scale alumina particles were added. When the fine-scale alumina particles were fully mixed with the cement, the larger-size (for example, 0.5-1.0 mm) alumina particles were added and mixed with the cement-alumina formulation. The viscosity of the final mix is another factor, as it must not be too low or too high. In addition, accelerants, and retarders can be used at selected points during the mold making process steps. Typical individual dispersing alumina with accelerants, and retarders include Almatis ADS-1, ADS-3, and ADW-1.

After mixing, the investment mix was poured in a controlled manner into a vessel that contains the fugitive wax pattern. The vessel provides the external geometry of the mold, and the fugitive pattern generates the internal geometry. The correct pour speed is a further feature, if it is too fast air can be entrapped in the mold, if it is too slow separation of the cement and the alumina particulate can occur. Suitable pour speed range from about 1 to about 20 liters per minute. In one embodiment, the pour speed is about 2 to about 6 liters per minute. In a specific embodiment, the pour speed is about 4 liters per minute.

In a second example, a slurry mixture for making an investment mold consisted of 3000 g of the calcium aluminate cement, (comprising approximately 10% by weight of mayenite, approximately 70% by weight of calcium monoaluminate, and approximately 20% by weight of calcium dialuminate), 1500 g of calcined alumina particles with a size of less than 10 microns, 2650 g of high-purity calcined alumina bubble of a size range from 0.5-1 mm diameter, 1650 g of deionized water, and 150 g of colloidal silica.

The alumina hollow particles provide a mold with a reduced density. The weight fraction of calcium aluminate cement is 42%, and that of the alumina is 58%. This formulation produced a mold that was approximately 125 mm diameter and 400 mm long. The mold was then cured and fired at high temperature. The produced mold was used for casting titanium aluminide-containing articles such as turbine blades with a good surface finish. The roughness (Ra) value was less than 100, and with an oxygen content of less than 2000 ppm. This formulation produced a mold that had a density of less than 1.8 grams per cubic centimeter.

In a third example, a slurry mixture for making an investment mold consisted of 600 g of the calcium aluminate cement, (consisting of approximately 10% by weight of mayenite, approximately 70% by weight of calcium monoaluminate, and approximately 20% by weight of calcium dialuminate), 300 g of calcined alumina particles with a size of less than 10 microns, 490 g of high-purity calcined alumina bubble of a size range from 0.5-1 mm diameter, 305 g of deionized water, and 31 g of colloidal silica. This formulation produced a smaller mold for a smaller component that was approximately 120 mm diameter and 150 mm long. The mold was then cured and fired at high temperature. The produced mold was used for casting titanium aluminide-containing articles such as turbine blades with a good surface finish. The roughness (Ra) value was less than 100 microinches, and with an oxygen content of less than 1600 ppm.

In a fourth example, a slurry mixture for making an investment mold consisted of 2708 g of the calcium aluminate cement, (comprising approximately 10% by weight of mayenite, approximately 70% by weight of calcium monoaluminate, and approximately 20% by weight of calcium dialuminate), 1472 g of high-purity calcined alumina bubble of a size range from 0.5-1 mm diameter, 1061 g of deionized water, and 196 g of colloidal silica. This formulation produced a smaller mold with a smaller alumina content for a smaller component. The mold was then cured and fired at high temperature. The produced mold was used for casting titanium aluminide-containing articles such as turbine blades.

The colloidal silica controls the rate of reaction of the calcium aluminate phases with water, and provides mold strength during curing. This rate of reaction of the calcium aluminate phases with water controls the working time of the investment mold mix during mold making. This time was between about 30 seconds and about 10 minutes. If the working time of the investment mold mix is too short, there is insufficient time to make large molds of complex-shaped components. If the working time of the investment mold mix is too long and the calcium aluminate cement does not cure sufficiently quickly, separation of the fine-scale cement and the large scale alumina can occur and this can lead to a segregated mold in which the formulation varies and the resulting mold properties are not uniform.

The three phases in the calcium aluminate cement comprise calcium monoaluminate ($CaAl_2O_4$), calcium dialuminate ($CaAl_4O_7$), and mayenite ($Ca_{12}Al_{14}O_{33}$), and the inventors made this selection to achieve several purposes. First, the phases must dissolve or partially dissolve and form a suspension that can support all the aggregate phases in the subsequent investment mold making slurry. Second, the phases must promote setting or curing of the mold after pouring. Third, the phases must provide strength to the mold during and after casting. Fourth, the phases must exhibit minimum reaction with the titanium alloys that is cast in the mold. Fifth, the mold must have a suitable thermal expansion match with the titanium alloy casting in order to minimize the thermal stress on the part that is generated during post-solidification cooling.

Figure 7:
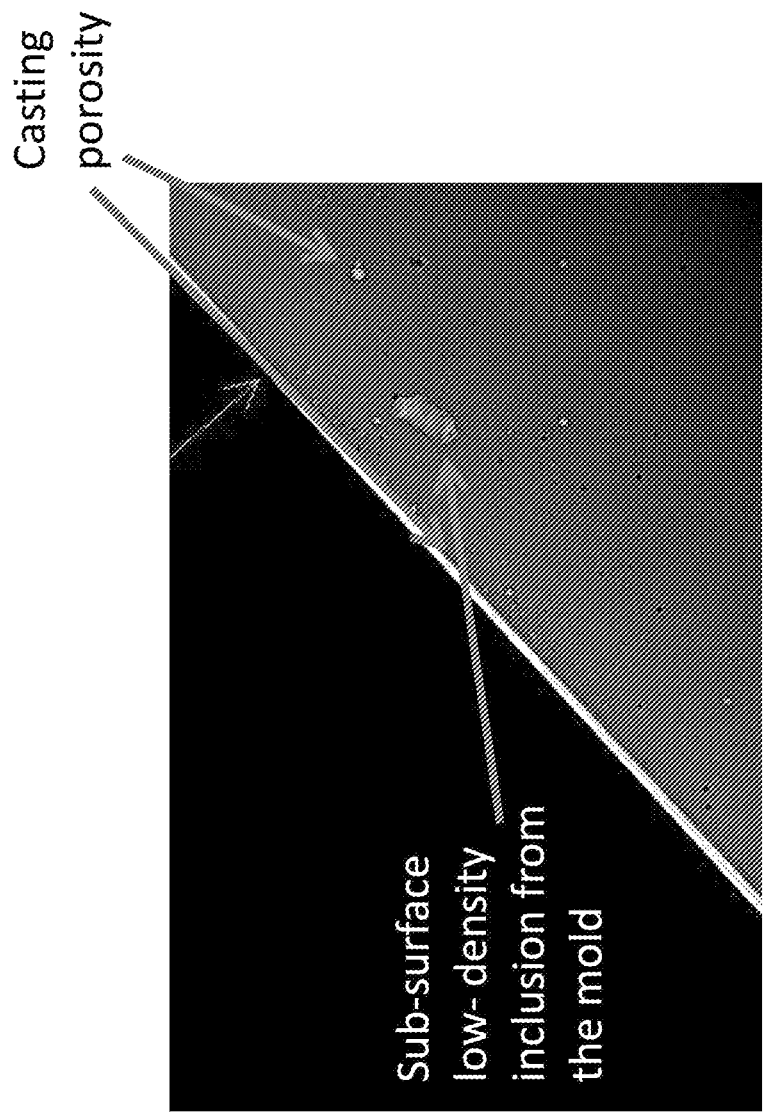
FIG. 7 shows X-ray images in planar view of a cast titanium aluminide article.
Figure 7:
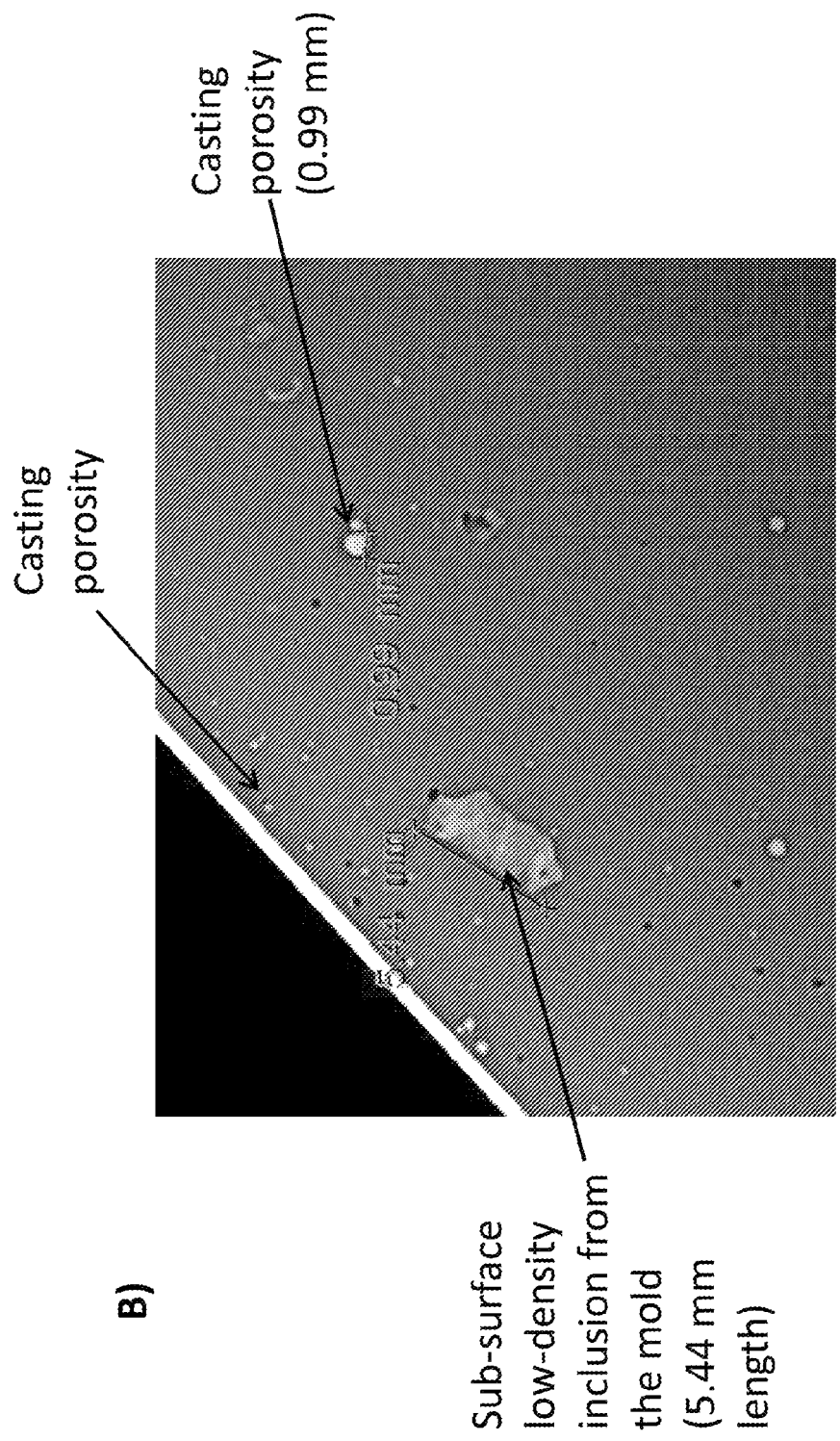
Figure 8:
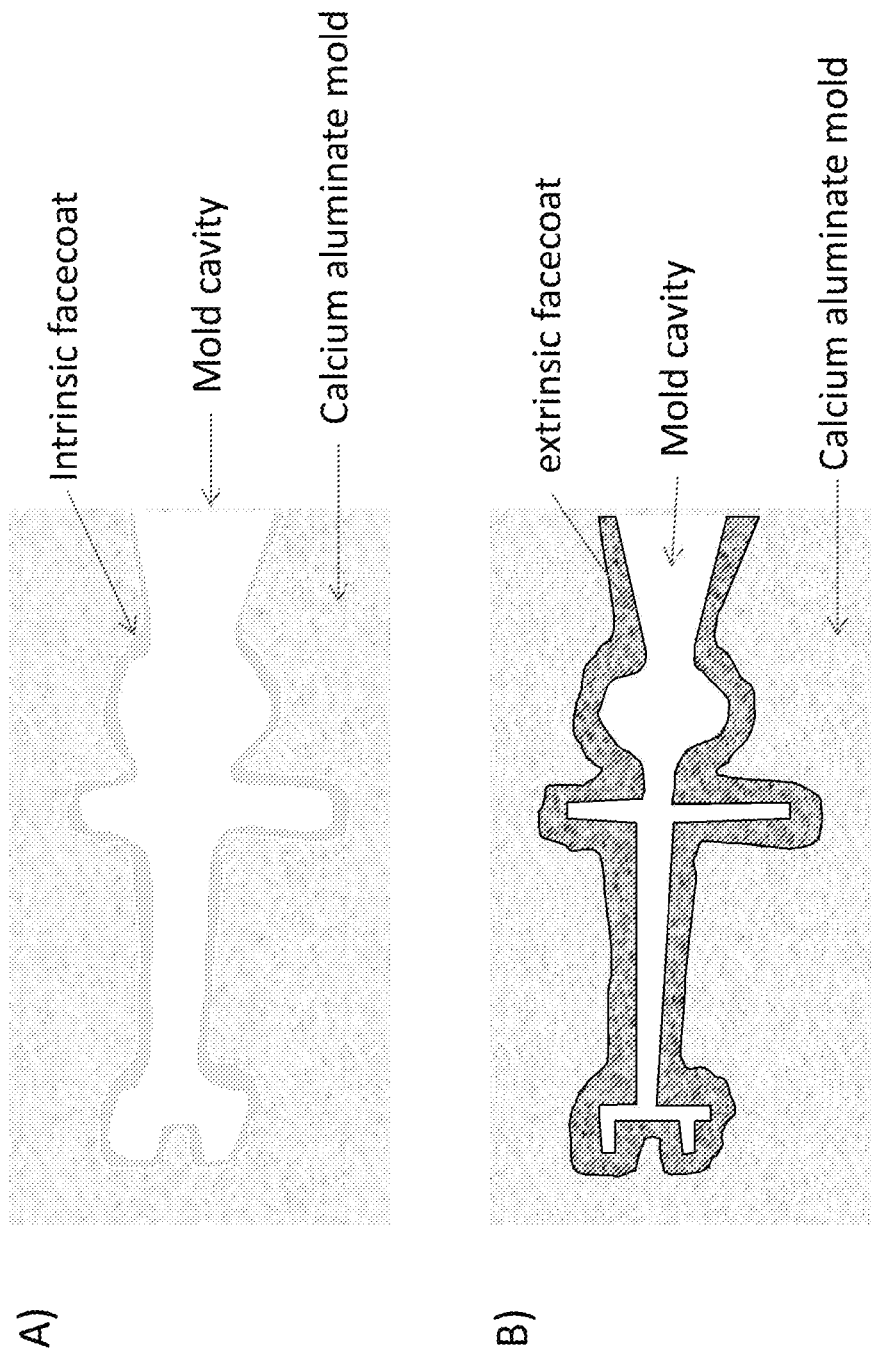
FIG. 8 shows a schematic of the mold with the facecoat.

The X-ray image (FIG. 7) shows a cast titanium aluminide blade that contains a sub-surface inclusion from calcium aluminate mold. This is a very large inclusion (5.44 mm) and can be resolved with digital enhancing techniques. Smaller low density inclusions from calcium aluminate mold are more difficult to resolve. In one aspect of the disclosure, the inventors used mold additions that increase the X-ray density of the mold in order to improve the inclusion detection capability.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure. It is to be understood that not necessarily all such objects or advantages described above may be achieved in accordance with any particular embodiment. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

While the disclosure has been described in detail in connection with only a limited number of embodiments, it should be readily understood that the disclosure is not limited to such disclosed embodiments. Rather, the disclosure can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims. All publications, patents, and patent applications mentioned herein are hereby incorporated by reference in their entirety as if each individual publication or patent was specifically and individually indicated to be incorporated by reference. In case of conflict, the present application, including any definitions herein, will control.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A method for detecting sub-surface ceramic inclusions in a titanium or titanium alloy casting, said method comprising:
   combining calcium aluminate, aluminosilicates, calcium aluminosilicates, and at least one element more radiographically dense than the calcium aluminate, and a liquid to form a slurry, wherein the aluminosilicates and calcium aluminosilicates are less than about 5% by weight;
   forming a mold from the slurry;
   introducing a titanium aluminide-containing metal to the mold;
   solidifying said titanium aluminide-containing metal to form an article in the mold;
   removing the solidified titanium aluminide-containing metal article from said mold;
   subjecting the solidified titanium aluminide-containing article to radiographic inspection to provide a radiograph; and
   examining said radiograph for the presence of the radiographically dense element on or in the article.

2. The method as recited in claim 1, further comprising removing the radiographically dense element from the article.

3. The method as recited in claim 2, wherein removing the radiographically dense element from the article comprises one or more of machining, grinding, polishing, or welding.

4. The method as recited in claim 1, wherein the combining further comprises combining oxide particles with the slurry.

5. The method as recited in claim 4, wherein said oxide particles comprise at least one of aluminum oxide particles, magnesium oxide particles, calcium oxide particles, zirconium oxide particles, and titanium oxide particles.

6. The method as recited in claim 4, wherein said oxide particles are aluminum oxide particles.

7. The method as recited in claim 4, wherein the element is more radiographically dense than the oxide particles.

8. The method as recited in claim 4, wherein the oxide particles comprise hollow oxide particles.

9. The method as recited in claim 8, wherein the hollow oxide particles comprise hollow aluminum oxide particles.

10. The method as recited in claim 1, wherein the element more radiographically dense than the calcium aluminate comprises ytterbium, hafnium, gadolinium, tungsten, thorium, uranium, yttrium, dysprosium, erbium, cerium and combinations thereof.

11. The method as recited in claim 1, wherein the titanium-containing cast article comprises a turbine blade.

12. The method as recited in claim 1, wherein the titanium-containing cast article comprises a titanium aluminide turbine blade.

13. The method as recited in claim 1, further comprising minimizing the presence of mold material inclusions in titanium aluminide-containing cast articles.

14. The method as recited in claim 1, wherein said calcium aluminate cement comprises less than about 70% alumina.

15. The method as recited in claim 1, further comprising forming an intrinsic facecoat of less than about 100 microns in said mold.

16. The method as recited in claim 1, further comprising forming the mold devoid of an extrinsic facecoat.

17. The method as recited in claim 1, wherein said at least one element more radiographically dense than the calcium aluminate is an X-ray or Neutron-ray detectable element in a range of about 1 to about 4 weight percent in the slurry.

18. The method as recited in claim 1, wherein said calcium aluminate cement comprises calcium monoaluminate, calcium dialuminate, and mayenite, wherein the calcium aluminate cement is greater than 30% by weight of the slurry.

19. The method as recited in claim 1, wherein said mold comprises impurities of less than about 2%, wherein the impurities comprise $Na_2O$, $SiO_2$, $Fe_2O_3$, and $TiO_2$, and combinations thereof.

* * * * *